United States Patent [19]
Prohaska

[11] Patent Number: 4,682,602
[45] Date of Patent: Jul. 28, 1987

[54] PROBE FOR MEDICAL APPLICATION

[75] Inventor: Otto Prohaska, Ann Arbor, Mich.

[73] Assignee: Ottosensor Corporation, Los Angeles, Calif.

[21] Appl. No.: 748,231

[22] Filed: Jun. 24, 1985

Related U.S. Application Data

[63] Continuation-in-part of Ser. No. 373,207, Apr. 29, 1982, abandoned.

[30] Foreign Application Priority Data

May 7, 1981 [AT] Austria ............... 2029/81

[51] Int. Cl.⁴ ............... A61B 5/00; A61B 5/04; A61N 1/05
[52] U.S. Cl. ............... 128/635; 128/642; 128/784; 128/803; 204/403
[58] Field of Search ............... 128/635, 639–642, 128/784, 803; 204/403, 414

[56] References Cited

U.S. PATENT DOCUMENTS

| | | | |
|---|---|---|---|
| 3,476,670 | 11/1969 | Weiner | 204/295 |
| 3,572,322 | 3/1971 | Wade | 128/2.06 |
| 3,590,810 | 7/1971 | Kopecky | 128/640 |
| 3,689,393 | 9/1972 | Davis | 204/195 |
| 4,082,087 | 4/1978 | Howson | 128/2.06 |
| 4,522,211 | 6/1985 | Bare et al. | 128/640 |

FOREIGN PATENT DOCUMENTS 342189 3/1978 Austria .
2425641 12/1975 France ............... 128/635

OTHER PUBLICATIONS

Prohaska et al., "A Multi-Electrode for Intracortical Recordings Produced by Thin-Film Technology", EEG & Clin. Neuro, 42, No. 3, 421–422, Mar. 1977.

Primary Examiner—Lee S. Cohen
Attorney, Agent, or Firm—John C. Purdue

[57] ABSTRACT

A medical probe having at least one transducer or electrode for registering or influencing tissue activities is disclosed. The probe comprises a substrate having a supporting surface and a cover layer which, together, form a chamber bounded on one side by the supporting surface and on an opposed side by a wall of the cover layer. The electrode or transducer is carried on the supporting surface of the substrate. An aperture in the wall of the cover layer provides communication between the exterior of the probe and the chamber. The probe is extremely accurate and selective, and extraneous signals which made prior art probes inaccurate do not detract from the accuracy of probes according to the instant invention.

24 Claims, 7 Drawing Figures

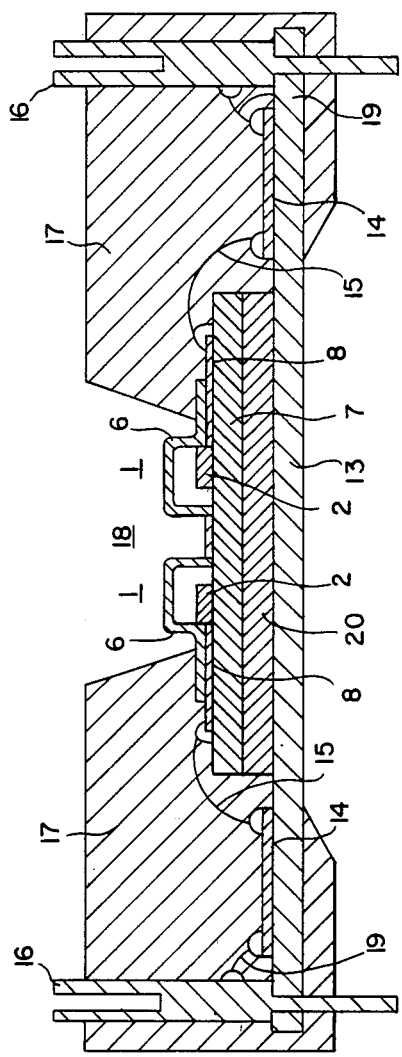
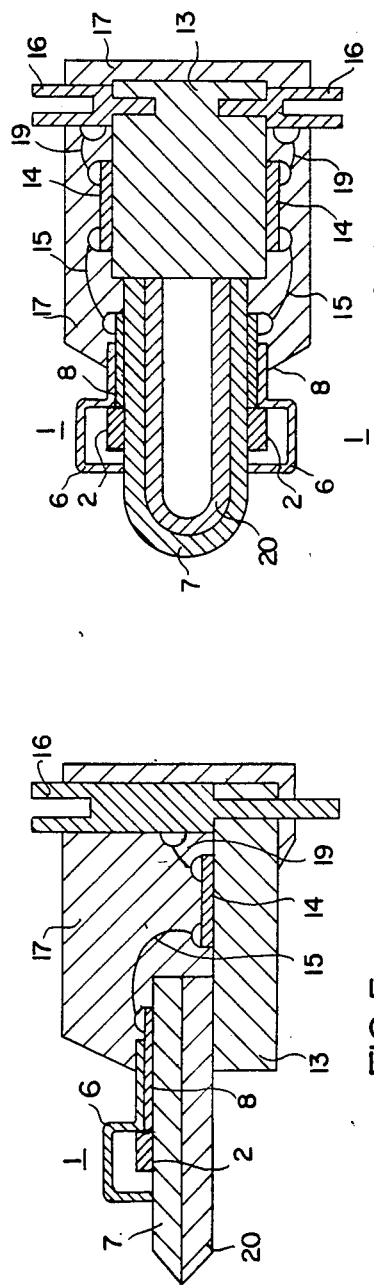

PROBE FOR MEDICAL APPLICATION

REFERENCE TO RELATED APPLICATION

This is a continuation-in-part of application Ser. No. 373,207, filed Apr. 29, 1982, now abandoned.

BACKGROUND

This invention is concerned with a medical probe for use in registering and influencing tissue activities. Especially meaningful are the thin film probes, called electrode probes or transducer probes, used in medical research as well as in human medicine in order to determine or to influence electrical activities of the tissue, metabolic activities, blood flow, ion and molecular changes, etc.

Thin film probes are qualified in particular for multiple recordings because of their possible variation in design and dimension (O. Prohaska, F. Pacha, P. Pfundner, H. Petsche: A-16-fold semi-microelectrode for intracortical recording of field potentials, Electroenceph. Clin. Neurophysiol. 47, 629–621, 1979).

One previously known medical electrode, disclosed in Austrian Patent No. 342,189, consists of a non-conducting body that carries on one end a contact electrode which is connected to a lead within the non-conducting body. In addition, a throw-away enclosure of non-conducting material is mounted around the individual reusable electrode. Within the cover is a cavity which borders on the contact electrode as well as on the outer area by at least one aperture in the throw-away enclosure and is filled by a viscous electrolyte. This type of structure provides for direct contact between the material under test and the metal or intermetallic compound electrodes and/or transducers which cause some serious disadvantages:

(a) the electrode impedance varies as an inverse function of the electrode area (H. J. Vetter: Elektrochemische Kinetik, Springer Verl. Berlin, 1961) and, therefore, miniaturization of the electrode(s) results in unacceptably high electrode impedance;

(b) polarographic recordings (I. M. Kolthoff, J. J. Lingane: Polarographie, Intersci, Publ. N.Y., 1952) cause a current flow through the tissue which irritates and, frequently, injures the tissue, (c) the extracellular ion and molecular concentration is only recordable under stable conditions which, unfortunately, seldom exist, (d) ion concentration changes in the material under test often alter potential recordings within the tissue; for instance: $Cl^-$-concentration changes cause the electrode potential change of an Ag/AgCl electrode to change.

SUMMARY OF THE INSTANT INVENTION

A probe according to the instant invention overcomes these disadvantages. The probe comprises at least one electrode or transducer (2) which is enclosed by an insulating cover (6) that is supported on an insulating substrate (7,11). The thickness of the cover is in the range of 0.5 μm up to 10 μm—preferably 3 μm. A chamber (1) is formed between the substrate (7,11) and the insulating cover (6). The chamber (1) can be up to 30 μm high (5) and is filled by a gaseous and/or fluid and/or solid medium (3) which provides communication between the electrode or transducer and at least one aperture (4). The insulating cover (6) is comprised of at least one of the materials SiO, $SiO_2$, $Si_3N_4$, $TiO_2$, $Ta_2O_5$ or similar materials which have mechanical or electrical properties comparable to the above-mentioned materials.

Significant new results are obtained by virtue of the fact that the chamber(s) (1) contain(s) a material, i.e., the medium (3), that establishes the contact between the electrode or transducer and the material under test (e.g., tissue). As a consequence, electrode impedance is reduced. In addition, in multi-electrode probes, the reference electrode is separated from the material under test, so that the potential of the reference electrode remains constant. In a probe according to the invention, through the use of thin film technology, one can incorporate a plurality of chambers whereby a plurality of parameters can be evaluated or influenced with a single probe.

For the purpose of illustrating the invention, there is shown in the drawings a form which is presently preferred; it being understood, however, that this invention is not limited to the precise arrangements and instrumentalities shown.

BRIEF DESCRIPTION OF THE DRAWINGS

FIGS. 4, 5, 6 and 7 are cross-sectional views showing four embodiments of probes according to the instant invention.

DETAILED DESCRIPTION OF THE INVENTION

Figure 1:
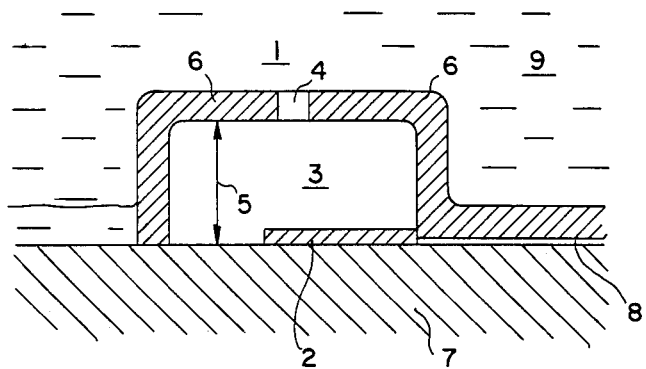
FIGS. 1, 2 and 3 are cross-sectional views showing three embodiments of chambers according to the instant invention.

FIG. 1 shows an elevated chamber (1) which is called a "thin film buffer chamber". Chamber (1) is defined by a thin insulating cover layer (6) which determines the outer shape of the thin film buffer chamber (1). Layer (6) is 0.5 μm to 10 μm thick, preferably 3 μm. The cover layer (6) may be composed of at least one of the following materials: $SiO_x$, $Si_3N_4$, $SiO_yN_z$, $TiO_2$, $Ta_2O_5$, where x is at least 1 but not greater than 2, y is greater than 0 and less than 2 and z is greater than 0 and less than 1.33. Materials similar to the named materials and having comparable mechanical or electrical properties may also be utilized. Layer (6) is directly supported on the insulating substrate (7) in such a way that it encloses at least one electrode or transducer (2).

Layer (6) has at least one aperture (4) which communicates between medium (3) and the material under test (9). In doing this, a new result was obtained: the aperture (4) represents now the actual electrode or transducer of the probe in forming the direct connection to the material under test (9), enabling a pointlike, local recording or influence. On the other hand, the metal or metal compound electrode (2) which was previously determining the qualities of the probe can be made much larger now since they are no longer in direct contact with the material under test (9) but only indirectly by means of the medium (3) within the thin film buffer chamber (1). In this way, the recording disturbances caused by the electrode impedance can be reduced up to 1000 times.

The property and shape of the insulating substrate (7) is widely variable. It can be stiff or pliable, round, uneven, flat, needle-shaped or cylindrical, etc.

Figure 2:
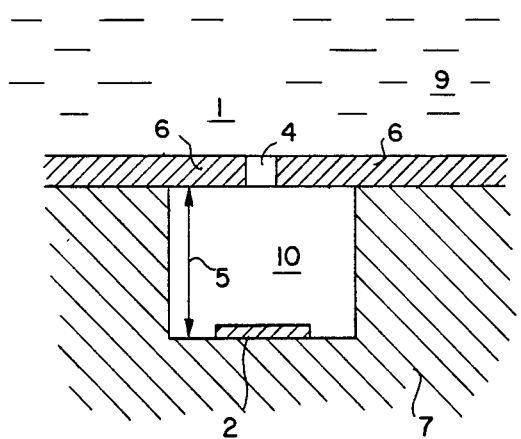

FIG. 2 shows another possible type of thin film buffer chamber (1) where the chamber shape is obtained by etching a recess (10) into the substrate (7). Cover layer (6) is flat. The probe is otherwise the same as that disclosed in FIG. 1.

Figure 3:
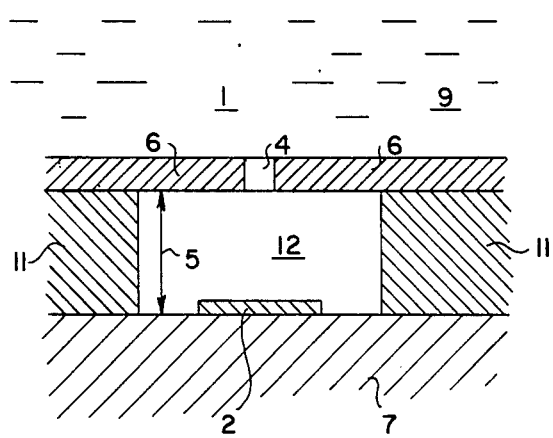

FIG. 3 demonstrates the chamber construction in a "sandwich design" where the recess (12) is etched into an insulation layer (11) which is supported by the substrate (7). In the versions of FIGS. 2 and 3, the recesses (10) or (12) are covered by a thin insulation layer (6) in which the aperture (4) is etched. The probe of FIG. 3 is otherwise the same as that disclosed in FIG. 1.

The advantages of a thin film version, using thin film technology methods for production, reside in the possibility of a very precise arrangement of several thin film chambers (1) within a very small area next to or above each other. This is extremely important for the practical application of the invention because the thin film version enables one to record or influence a parameter regardless of the structure of the tissue under test. Due to this precision as well as the multiple arrangement of the electrode and transducer areas, a new result is achieved—a connection between different activities and parameter changes of the tissue can be exhibited and a spatial resolution of the above-mentioned processes can be demonstrated, yielding completely new results.

The medium (3) within the thin film buffer chamber (1) determines the identity of the recordable or influencable parameters. The medium (3) can consist of gaseous and/or liquid and/or solid material, for instance an electrolyte, an enzyme, an ion exchanger or any combination thereof. In order to be operable in the instant invention, the medium need only contain a material which is capable of registering or influencing a measurable signal which changes as a function of changes in a property, including optical properties, of the material being tested. Numerous electrolytes are known in the art and many of them are polymers. The properties of the material under test and the activities thereof which are to be registered or influenced will dictate, to a large extent, the choice of a particular medium, in conjunction with other factors which are well known to those skilled in the art. In the case where the chamber (1) is filled with a medium (3) which reacts with the material under test, such as an enzyme or an ion exchanger, there is a reservoir of that medium (3) in the chamber (1). As a consequence, the medium does not need to be replenished nearly as often as would be necessary in prior art probes. Just as important for the recording or influencing mode is the selection of the electrode or transducer materials (2), which may be composed of a precious metal, preferably gold or platinum, or a semi-conductor, or intermetallic compounds or metal salts, a suitable one being Ag/AgCl. They could also function as a thermocouple or a resistance thermometer. Alternatively, at least two electrodes or transducers (2) can be utilized to form an electrochemical cell together with the medium (3). In doing this, an essentially new result is yielded: the current, caused by voltommetric recordings, flows within the "thin film buffer chamber" (1) and does not influence the material under test in an undesired way.

One embodiment of the thin film buffer chamber probe is shown in FIG. 4. Thereby, the insulating substrate (7), due to easy application or performance, might be mounted on an additional insulating and/or conducting supplementary substrate (20), preferably supported on an insulating carrier (13) on which conductors (14) are arranged. The conductors (8) on the insulating substrate (7) are electrically connected (15) with the conductors (14) on the carrier (13). In order to guarantee a simple, fast and reliable electrical contact to the conductors (14) and (8) and therewith to the electrode or transducer (2) within the thin film buffer chambers (1), contact plugs (16) are mounted on the insulating carrier (13) in such a way that they are connected electrically (19) with the conductors (14). By appropriate casting of the described arrangement with insulating materials (17), preferably synthetic plastic resin or the like, a container (18) is formed by the insulating material (17) and the insulating substrate (7) on top of which the thin film buffer chambers (1) are situated. The container (18) is open upwardly and can be sealed arbitrarily. This type of process is especially suitable for investigations of tissue cultures, which are placed into the container (18). The probe is otherwise the same.

Another embodiment of the thin film buffer chamber probe is shown in cross section in FIG. 5. The insulating substrate (7) has a needle-like shape. The insulating substrate (7) is supported on an insulating and/or conducting additional substrate (20) which has the same needle-like shape as the insulating substrate (7). In this way, tissue damage is prevented. By the insulating material (17), the non-insulated parts of the conductors (8) and (14) are poured in as well as the electrical connections (15) and (19). The probe is otherwise the same.

An additional embodiment of the instant invention is shown in FIG. 6. The insulating substrate (7) or the insulating and/or conducting additional substrate (20) has a cylindrical shape. All other features are the same as those described in connection with FIG. 5.

FIGS. 5 and 6 show probe types which are especially suitable for investigation or the influencing of tissue areas located deeper within the body, i.e., deep brain structures subcutaneous tissue parts, etc.

Figure 7:
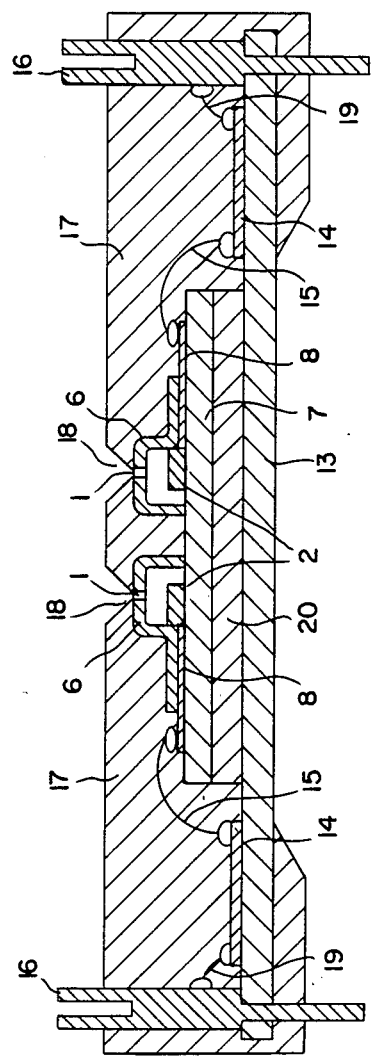

A variation of the probe in FIG. 4 is the probe type shown in FIG. 7. By embedding the described probe suitably in insulating material (17), this insulating material (17) forms containers (18) which are open in the upward direction, whereby the apertures (4) of the chambers (1) are kept free.

The present invention may be embodied in other specific forms without departing from the spirit or essential attributes thereof and, accordingly, reference should be made to the appended claims, rather than to the foregoing specification, as indicating the scope of the invention.

I claim;

1. A probe for registering or influencing tissue activities and properties of chemical samples comprising a substrate having a supporting surface; means including a cover layer having a thickness of 0.5 to 10 $\mu$m. carried on the supporting surface of said substrate, said means and a portion of the supporting surface of said substrate forming a chamber which is bounded on one side by the supporting surface and on an opposed side by a wall of said cover layer which is spaced from the supporting surface by not more than about 30 $\mu$m., the chamber being closed except for an aperture in the last-named wall which enables communication between the chamber and the exterior of the probe; an electrode or transducer which is substantially less than 30 $\mu$m. in thickness carried on the supporting surface of said substrate inside the chamber; means including a conductor mounted on the probe, inside the chamber, and operable to conduct a signal between said electrode or transducer and registering or influencing circuitry.

2. A probe in accordance with claim 1 wherein the chamber contains a medium which is an electrolyte.

3. A probe in accordance with claim 2 wherein the supporting surface of said substrate carries an electrode, and which additionally includes a second electrode which forms an electro-chemical cell with the electrolyte and the first of said electrodes.

4. A probe in accordance with claim 2 wherein the supporting surface of said substrate carries a transducer, and which additionally includes a second transducer which forms an electro-chemical cell with the electrolyte and the first of said transducers.

5. A probe in accordance with claim 1 wherein the chamber contains a medium which is an ion exchanger.

6. A probe in accordance with claim 5 wherein the supporting surface of said substrate carries an electrode, and which additionally includes a second electrode which forms an electro-chemical cell with the ion exchanger and the first of said electrodes.

7. A probe in accordance with claim 5 wherein the supporting surface of said substrate carries a transducer, and which additionally includes a second transducer which forms an electro-chemical cell with the ion exchanger and the first of said transducers.

8. A probe in accordance with claim 1 wherein the chamber contains a medium which is an enzyme.

9. A probe in accordance with claim 1 wherein said cover layer is composed of a material selected from the group consisting of $SiO_x$, $Si_3N_4$, $SiO_yN_z$, $TiO_2$ and $Ta_2O_5$, where x is at least 1 and not greater than 2, y is greater than 0 and less than 2 and z is greater than 0 and less than 1.33.

10. A probe for registering or influencing tissue activities and properties of chemical samples comprising a substrate having a supporting surface; a cover layer; means supporting said cover layer in a predetermined spaced relationship with the supporting surface of said substrate, said means, said cover layer and a portion of the supporting surface of said substrate forming a chamber which is bounded on one side by the supporting surface and on an opposed side by a wall of said cover layer which is spaced from the supporting surface, the chamber being closed except for an aperture in the last-named wall which enables communication between the chamber and the exterior of the probe, the supporting surface of said substrate being sufficiently large, relative to the size of the aperture, to accommodate an electrode or transducer sufficiently large to minimize recording disturbances; an electrode or transducer carried on the supporting surface of said substrate inside the chamber, said electrode or transducer being sufficiently large, relative to the size of the aperture, to minimize recording disturbances, and being in a predetermined position relative to the aperture; and means including a conductor mounted on the probe, inside the chamber, and operable to conduct a signal between said electrode or transducer and registering or influencing circuitry.

11. A probe in accordance with claim 10 wherein the chamber contains a gaseous, liquid or solid medium which comprises an electrolyte.

12. A probe in accordance with claim 11 wherein the supporting surface of said substrate carries an electrode, and which additionally includes a second electrode which forms an electro-chemical cell with the electrolyte and the first of said electrodes.

13. A probe in accordance with claim 11 wherein the supporting surface of said substrate carries a transducer, and which additionally includes a second transducer which forms an electro-chemical cell with the electrolyte and the first of said transducers.

14. A probe in accordance with claim 10 wherein the chamber contains a gaseous, liquid or solid medium which comprises an ion exchanger.

15. A probe in accordance with claim 14 wherein the supporting surface of said substrate carries an electrode, and which additionally includes a second electrode which forms an electro-chemical cell with said gaseous, liquid or solid medium and the first of said electrodes.

16. A probe in accordance with claim 14 wherein the supporting surface of said substrate carries a transducer, and which additionally includes a second transducer which forms an electro-chemical cell with said gaseous, liquid or solid medium and the first of said transducers.

17. A probe in accordance with claim 10 wherein the chamber contains a gaseous, liquid or solid medium which comprises an enzyme.

18. A probe in accordance with claim 17 wherein the supporting surface of said substrate carries an electrode, and which additionally includes a second electrode which forms an electro-chemical cell with said gaseous, liquid or solid medium and the first of said electrodes.

19. A probe in accordance with claim 17 wherein the supporting surface of said substrate carries a transducer, and which additionally includes a second transducer which forms an electro-chemical cell with said gaseous, liquid or solid medium and the first of said transducers.

20. A probe in accordance with claim 10 wherein said cover layer is composed of a material having the properties of one selected from the group consisting of $SiO_x$, $Si_3N_4$, $SiO_yN_z$, $TiO_2$ and $T_{a2}O_5$, where x is at least 1 and not greater than 2, y is greater than 0 and less than 2 and z is greater than 0 and less than 1.33.

21. A probe in accordance with claim 10 which additionally includes a second cover layer, means supporting said second cover layer in a predetermined spaced relationship with the supporting surface of said substrate, said means, said second cover layer and a portion of the supporting surface of said substrate forming a second chamber which is bounded on one side by the supporting surface and on an opposed side by a wall of said second cover layer which is spaced from the supporting surface, said second chamber being closed except for an aperture in the last-named wall which enables communication between the chamber and the exterior of the probe, an electrode or transducer carried on the supporting surface of said substrate inside said second chamber, means including a conductor mounted on the probe, inside the second chamber, and operable to conduct a signal between said electrode or transducer in the second chamber and registering or influencing circuitry.

22. A probe in accordance with claim 21 wherein the supporting surface of said substrate within the second chamber is sufficiently large, relative to the size of the aperture, to accommodate an electrode or transducer sufficiently large to minimize recording disturbances, and wherein said electrode or transducer in the second chamber is sufficiently large, relative to the size of the aperture, to minimize recording disturbances.

23. A probe for registering or influencing tissue activities and properties of chemical samples comprising a substrate having a supporting surface; a plurality of cover layers; means supporting each of said cover layers in a predetermined spaced relationship with the supporting surface of said substrate, said means, said cover layers and a portion of the supporting surface of said substrate forming a plurality of chambers, each of which is bounded on one side by the supporting surface and on an opposed side by a wall of said cover layer which is spaced from the supporting surface, each chamber being closed except for an aperture in the last-named wall which enables communication between the chamber and the exterior of the probe, the supporting surface of said substrate within each of the chambers being sufficiently large, relative to the size of the aperture, to accommodate an electrode or transducer sufficiently large to minimize recording disturbances; an electrode or transducer carried on the supporting surface of said substrate inside each of the chambers; means including a conductor mounted on the probe, inside each of the chambers, and operable to conduct a signal between each of said electrodes or transducers and registering or influencing circuitry.

24. A probe for registering or influencing tissue activities and properties of chemical samples comprising a substrate having a supporting surface; means including a plurality of cover layers carried in a predetermined spaced relationship on the supporting surface of said substrate, said means and a portion of the supporting surface of said substrate forming a plurality of chambers, each of which is bounded on one side by the supporting surface and on an opposed side by a wall of one of said cover layers which is spaced from the supporting surface, each chamber being closed except for an aperture in the last-named wall which enables communication between the chamber and the exterior of the probe; an electrode or transducer carried on the supporting surface of said substrate inside each of the chambers; means including a conductor mounted on the probe, inside each of the chambers, and operable to conduct a signal between each of said electrodes or transducers and registering or influencing circuitry.

* * * * *